United States Patent [19]

Gierthy

[11] Patent Number: 4,904,595
[45] Date of Patent: Feb. 27, 1990

[54] EPITHELIAL CELL LINE USEFUL IN THE DETECTION OF DIOXINLIKE COMPOUNDS AND METHODS OF MAKING AND USING SAME

[75] Inventor: John F. Gierthy, East Greenbush, N.Y.

[73] Assignee: Health Research Incorporated, Albany, N.Y.

[21] Appl. No.: 745,008

[22] Filed: Jun. 14, 1985

[51] Int. Cl.[4] .......................... C12N 5/00; C12Q 1/02
[52] U.S. Cl. .................................. 435/240.2; 435/29; 435/240.23; 435/948; 436/63; 436/815
[58] Field of Search ................. 435/240.2, 240.23, 29, 435/240.1, 948; 436/63, 815

[56] References Cited

U.S. PATENT DOCUMENTS 4,016,036 4/1977 Green et al. ......................... 195/1.8
4,569,916 2/1986 Penman et al. ......................... 436/64

OTHER PUBLICATIONS

Gierthy, J. F. et al., "Reversible Inhibition of In Vitro Epithelial Cell Proliferation by 2,3,7,8-Tetrachlorodibenzo-p-dioxin", *Toxicol. Appl. Pharmacol.*, 74:91-98, 1984.

Knutson, J. C., "Keratinization of Mouse Teratoma Cell Line XB Produced by 2,3,7,8-Tetrachlorodibenzo-p-dioxin: an in Vitro Model of Toxicity", *Cell* 22:27-36, Nov. 1980 (Part 1).

Rheinwald, J. G. et al., "Formation of a Keratinizing Epithelium in Culture by a Cloned Cell Line Derived from a Teratoma", *Cell* 6:317-330, Nov. 1985.

*Primary Examiner*—Margaret Moskowitz
*Assistant Examiner*—Kay E. Cheney
*Attorney, Agent, or Firm*—Curtis, Morris & Safford

[57] ABSTRACT

This invention relates to a novel epithelial cell line, a process for the preparation of the cell line, and its use in an in vitro bioassay for dioxinlike activity based on alterations in the cell line proliferation and morphology. The proprietary cell line of this invention exhibits a dioxin-induced, reversible, postconfluent inhibition of cell proliferation and a characteristic dioxin-induced flat-cell morphology.

13 Claims, 5 Drawing Sheets

M TCDD

EPITHELIAL CELL LINE USEFUL IN THE DETECTION OF DIOXINLIKE COMPOUNDS AND METHODS OF MAKING AND USING SAME

A deposit of this new cell line has been made to the American Type Culture Collection (ATCC), 12301 Parklawn Drive, Rockville, Md. 20852. The deposit was made on May 22, 1985 and was assigned number C-RL-8808.

FIELD OF THE INVENTION

This invention relates to the detection of certain toxic compounds and, more specifically, to a novel epithelial cell line (ATCC depository accession number CRL 8808), also called the "XBF" cell line, and its use in an in vitro bioassay. The cell line exhibits specific biological activity consistent with the presence of the most toxic dioxin congeners and isomers, i.e. "dioxinlike compounds". This activity, referred to as "dioxinlike" activity, induced by the presence of dioxinlike compounds consists of alterations in the proliferation and morphology of the novel epithelial cell line, which is referred to as the "flat-cell effect".

BACKGROUND OF THE INVENTION

The occurence of polychlorinated dibenzo-p-dioxins (PCDD) and dibenzofurans (PCDF) in the environment and the workplace poses a serious potential threat to human health. These compounds are among the most toxic and teratogenic low molecular weight compounds known.

Chlorinated dibenzo-p-dioxins are formed from the condensation of two orthochlorophenates under conditions of high alkalinity, pressure and temperature. 2,3,7,8-tetrachlorodibenzo-p-dioxin (TCDD) is formed as a contaminant by the condensation of two trichlorophenate molecules in the production of the herbicide 2,4,5-T. Synthesis of polychlorinated biphenyls (PCBs) can also produce chlorinated dibenzofurans as contaminants and various chlorinated dibenzo-p-dioxin isomers are formed in the commercial production of pentachlorophenol.

Burning of organic compounds, under appropriate conditions of temperature of combustion, chemical nature and combustion chamber residence time can also lead to the production of PCDDs and PCDFs. This has been verified by the analysis of flue gas emission and fly ash of municipal incinerators in the Netherlands. This phenomenon has also been observed in laboratory models. The pyrolysis of organohalogens such as chlorinated phenols and PCBs leads to the formation of PCDDs and PCDFs.

The PCDDs consist of 75 isomers and congeners which vary in the number and position of the chlorines. One of the most toxic, TCDD is a nearly planar tricyclic aromatic molecule. It is very stable in soil, has few readily reactive groups and is very insoluble in water ($6 \times 10^{-10}$ M). The toxicity of these compounds has been shown to be dependent upon the number and location of the chlorines, with TCDD being the most toxic isomer, with an oral $LD_{50}$ for guinea pigs of 1 $\mu$g/kg. TCDD is considered to be one of the most potent low molecular weight molecule known, with a minimum lethal dose orders of magnitude below sodium cyanide, strychnine and curare. In contrast to these agents, which are fast-acting, a single dose of TCDD may result in death weeks later. Species susceptibility to TCDD varies, with the hamster being 5,000 times less sensitive than the guinea pig. The exact cause of death is unknown. Hepatic necrosis may be involved in rats, rabbits and mice, but not in guinea pigs.

Many of the studies leading to present knowledge of the toxicity associated with PCDDs and PCDFs were initiated in response to specific poisoning episodes. The occurence of these compounds as a contaminant in chlorophenols which were used in hide curing led to an outbreak of chick edema in this country in 1957. It was determined that contaminated fat removed from the hides was being used as chicken feed. Hydropericardium as well as kidney and liver damage of the poultry were described.

The effects of human exposures have been seen in a number of industrial processing plant incidents. An acne outbreak in Germany in 1954 was traced to trichlorophenol contaminated with PCDDs and PCDFs. Similar outbreaks of chloracne were noted in 2,4,5-T production plants in France, Germany and the United States in the 1950's and 1960's. In 1971 the use of waste oil contaminated with TCDD for dust control in a riding arena led to the death of a large number of horses and other small animals, as well as chloracne in children who played in the area. The contamination by dibenzofuran analogs of rice oil in Japan led to many cases of chloracne. The explosion of a chemical plant in Seveso, Italy in 1976 led to TCDD exposure and was thought to be responsible for the occurrence of chloracne in humans as well as a number of livestock losses. The use of Agent Orange (a mixture of n-butyl esters of 2,4-D and 2,4,5-T), a defoliant, in Vietnam between 1962 and 1969 led to the contamination of large areas by TCDD.

Animal studies have demonstrated the pleomorphic nature of TCDD toxicity. These include prolonged wasting syndrome prior to death, lymphoid involution and embryotoxicity and or teratogenicity, hyperkeratoses and chloracne, edema, hyperplasia of the epithelium of the stomach, intestines and urinary bladder, hepatocellular damage and thymic involution. Acneform lesions are the most common known toxic manifestation of TCDD exposure in humans. This response is thought to be caused by a thickening of the epidermis (acanthosis), hyperkeratosis and metaplastic change in the sebaceous glands to a squamous epithelium. Chloracne results as the keratinaceous material plugs hair follicles and the sebaceous glands become cystic.

Since the health hazards associated with these toxic compounds are of major public concern, a rapid, accurate and inexpensive means of detecting such compounds is of great importance. Unfortunately, a simple means of detecting these compounds has proven to be a long-standing and significant problem in the art.

In the past, it has been shown that TCDD and its congeners can induce aminolevulinic acid synthetase, which is the initial and rate limiting enzyme of heme synthesis which is correlated with the occurence of hepatic porphyria in animals, and aryl hydrocarbon hydroxylase (AHH) which is a cytochrome P-450 microsomal monoxygenase used for detoxification of xenobiotics and implicated in the activation of many procarcinogens to ultimate carcinogens. Further work using AHH responsive and non-responsive inbred strains of mice showed that the ability to express this enzyme induction is inherited as an autosomal dominant at the Ah locus with TCDD being about 30,000 times as potent as 3-methylcholanthrene. It was also postulated and later demonstrated that a TCDD receptor species exists and can be isolated in the cytosol fraction of mouse livers. This led to the development of a TCDD competitive binding procedure which allowed the affinity of TCDD binding with this receptor site to be compared to that of its isomers and congeners.

The in vivo induction of the hyperkeratinization response to TCDD exposure in an in vitro model system has been demonstrated by Knutson and Poland, Cell 22, 27-36 (1980). This hyperkeratinization response is thought to be responsible for the occurence of chloracne. It was found that TCDD did not produce an acute toxic response in 23 various cell cultures as judged by cell growth, viability and morphology. It was shown, however, that "XB" cells, derived as a cloned epithelial cell line from a mouse teratoma, in co-culture with irradiated 3T3 cells would exhibit a keratinization response to TCDD exposure when grown at high cell density. High density XB/3T3 cultures not treated with TCDD did not show this response.

Keratinization was induced in the XB/3T3 system at a concentration as low as 3.2 pg of TCDD per ml. This model is particularly relevant since it deals with an induced differentiation of the intact cell using an endpoint (hyperkeratinization) known to be relevant to human exposure, i.e. chloracne.

A correlation has been demonstrated between the degree of toxicity of TCDD isomers and congeners and the extent of enzyme induction, receptor binding and hyperkeratinization response. Certain chemical structural characteristics have been related to toxic potential and other measured parameters. These are as follows: (1) that potent inducers of these biological effects have halogen atoms located at three of the four lateral ring positions (2,3,7,8); (2) that at least one ring position is nonhalogenated; (3) the order of potency of halogenated substitution is $Br>Cl>F$; (4) the molecule must maintain a rigid planar geometry for maximal potency. This geometry must be tricyclic (furans, dioxins, azobenzenes, aniline, etc.) or bicyclic but bridged such as PCBs and biphenylenes. The configuration for potency must be a $3\text{Å}\times 10\text{Å}$ rectangle and modulation of potency from inactive, through low level to high level is dependent on the positions halogenated.

The toxicological effects of these structural characteristics cannot be discerned by methods of chemical analysis alone but must be expressed in an intact biological system. There are 22 possible TCDD isomers alone and precise analysis requires their availability as standard as well as their separation by a high resolution analytical technique such as HPLC, gas chromatography and mass spectrometry, which techniques are not amenable for routine analytical screening.

A bioassay, which is based on an intact living system, is needed as a broad screen for the detection of the biological activity consistent with that of the most toxic dioxin congeners and isomers. Such an assay could be used to determine the relative potency of individual pure compounds or of the aggregate potency of mixtures of compounds as in complex enviornmental samples.

Attempts to develop an in vitro bioassay for dioxinlike activity have verified the induction of keratinization in the XB/3T3 cell system by TCDD and have further demonstrated its potential usefulness in the semiquantitative detection of this activity in extracts of environmental samples. See Gierthy and Crane, J. Toxicology and Applied Pharmacology, 74, 91-98 (1984). The relative potency of these samples correlated well with the relative contamination of the samples by PCDFs. However, keratinization induction is not useful in practice due to the instability of the trait in the XB target cells. Utilization of this trait in a simple in vitro bioassay is therefore impossible, due to the complications that arise from the necessity of initiating repeated new cell cultures.

OBJECTS OF THE INVENTION

It is an object of the invention to provide an epithelial cell line which is useful in detection of dioxinlike compounds due to the exhibition by the cell line of a stable characteristic response when in the presence of said compounds.

It is another object of the invention to provide a method of producing an epithelial cell line useful in the detection of dioxinlike compounds.

It is also an object of the invention to provide a method of detecting dioxinlike compounds by means of a rapid, inexpensive screening bioassay using an epithelial cell line which exhibits a stable characteristic response when in the presence of said compounds.

It is a further object of the invention to provide a bioassay which is capable of separating environmental samples which do not cause dioxinlike activity and therefore eliminating the need for those samples to undergo expensive chemical analysis.

It is still another object of the invention to provide a bioassay which allows for the detection of a broad spectrum of chemicals, all of which possess varying amounts of dioxinlike activity.

It is yet another object of the invention to provide a bioassay which is capable of providing an indication of the aggregate toxicity of a sample as regards the dioxinlike activity induced by a sample which contains a number of chemicals of varying potencies.

It is also an object of the invention to provide a bioassay which allows for priority ranking of many samples, permitting more discriminating use of the limited high resolution chemical analysis facilities for the identification and quantitation of the active components.

It is still another object of the invention to provide a bioassay which is capable of the detection in environmental samples of compounds which induce dioxinlike activity but whose presence is not being specifically assessed for by chemical analysis for the specific compounds.

It is another object of the invention to provide a means for the determination of the potency with regards to the dioxinlike activity induced by "suspect" compounds, for example, structural analogs of known toxic compounds.

It is still another object of the invention to provide of means of detecting the acnegenic activity of commercial compounds, for example, cosmetic ingredients, which means can be used as an alternative to animal testing.

Various other objects, advantages and features of the present invention will be readily apparent from the ensuing detailed description and the novel features will be particularly pointed out in the appended claims.

These and other objects are met by the present invention.

SUMMARY OF THE INVENTION

The present invention is directed, inter alia, to a stable non-keratinizing derivative of an XB epithelial cell line which required coculture with lethally irradiated mouse fibroblasts (3T3), which was cloned from mouse teratoma by Rheinwald and Green as taught in Cell 6, 317–330, 1975.

The inventive cell line may be referred to hereinafter as an XBF cell line.

In accordance with this invention, I have observed a change in the XB phenotype and have determined that, under my conditions of cell culture, late-passage XBF cells no longer keratinize upon exposure to TCDD although they continue to proliferate and to grow to a higher density than the early-passage XB cells.

The inventive XBF cell line, when cocultured with lethally irradiated 3T3 cells, or other appropriate non-proliferating fibroblast cells, or other appropriate non-proliferating fibroblast cells, or medium conditioned by such cells in a proliferating or non-proliferating state, (XBF/3T3 culture) grows to higher saturation density than the original XB line grown under similar conditions and exhibits a fusiform morphology at said high density. When the subconfluent XBF/3T3 cultures are exposed to dioxinlike compounds, certain characteristics are exhibited. There is a reversible, postconfluent inhibition of cell proliferation, or low saturation density, along with a change in morphology, the cells exhibiting a flat, cobblestone-like morphology ("flat-cell effect" or "flat-cell activity"), as compared to XBF/3T3 control cultures, not treated with dioxinlike compounds, which exhibit high saturation density fusiform morphology.

This XBF/3T3 phenotype is stable for over a year of routine culturing, unlike the XB/3T3 culture system, which rapidly loses its dioxinlike compound induced keratinization characteristic under similar conditions.

The sensitivity and stability of the XBF/3T3 flat-cell effect for TCDD as described herein identifies a novel XBF cell line that can be employed in a unique bioassay ("flat-cell assay") for determining the presence of dioxinlike compounds in environmental samples.

The relative specificity and sensitivity of the XBF/3T3 cell lines for TCDD—and the agreement of the results obtained by the biologic and chemical methods reported herein (see the specific Examples, for the soot extracts contaminated with PCDFs and PCDDs)—support the finding that the XBF/3T3 cell line and the assay described herein are useful alternatives or supplements to expensive chemical analysis. The flat-cell assay described herein is useful for screening many samples, reserving any subsequent high-resolution chemical analysis for samples which demonstrate dioxinlike activity.

The novel phenotype of XBF cells has been found to respond to very low levels of TCDD by an increased sensitivity to density-dependent inhibition of replication (DDIR) and the appearance of a flat epithelial morphology, as compared to the fusiform morphology of high-density nonexposed replicate cultures. TCDD, at a minimal concentration of $10^{-11}$ M, induces both a morphologic change and reversible inhibition of post-confluent cell proliferation in the XBF/3T3 system of this invention. This TCDD-induced decrease in saturation density observed in the XBF/3T3 cultures does not result from a general toxic response and is reversible.

The morphologic change induced by TCDD in these cultures is characterized by the appearance of flat, cobblestone like cells (referred to herein as the "flat-cell" effect), as compared to the fusiform, high-density XBF/3T3 control cultures.

Studies using inhibitors of macromolecular synthesis and mitosis indicate that the morphologic change seen in postconfluent cultures is not simply a consequence of inhibition of cell division. Other compounds, such as PCBs and certain PAHs, demonstrate relatively little potential for inducing this activity. Ranking of the flat-cell-inducing potentials of these chemicals also suggests a structure-activity relationship which is consistent with those of the keratinization system, TCDD receptor binding, AHH induction, and animal toxicity.

The XBF/3T3 phenotype of this invention is more stable than the induction of keratinization of XB cells during extended serial culture and therefore is more useful as an indicator of the presence of dioxinlike compounds.

In the following section, the invention is described in greater detail to illustrate several of its embodiments.

SUMMARY OF CERTAIN PREFERRED EMBODIMENTS

In accordance with this invention I have found that a dioxinlike compound, for example, tetrachlorodibenzo-p-dioxin (TCDD) induces changes in morphology and proliferation characteristics of certain cells, for example, a nonkeratinizing derivative (XBF or ATCC CRL 8808) of a keratinizing epithelial cell line (XB), cloned from a mouse teratoma, when the cells are propagated or cultured with certain propagating or culturing means. The propagating or culturing means can be non-proliferating fibroblast cells or medium conditioned by either non-proliferating fibroblast cells or proliferating fibroblast cells. The non-proliferating fibroblast cells may be, for example, lethally irradiated 3T3 cells; proliferating fibroblast cells may be, for example, non-irradiated 3T3 cells. Further, in accordance with this invention, detection of dioxinlike activity in XBF/3T3 cultures caused by TCDD in various types of environmental samples and polutants has indicated that the novel XBF cell line of this invention can be used to determine the activities of other materials. For example tests of polychlorinated dibenzodioxins (PCDDs), polychlorinated dibenzofurans (PCDFs), polychlorinated biphenyls (PCBs), polynuclear aromatic hydrocarbons (PAHs), and pesticides for their ability to induce these effects are described herein. These test results indicate that, for the representative compounds tested, the changes in morphology and proliferation of the XBF cell line is relatively specific for—and that the XBF cells are extremely sensitive to—the most toxic PCDDs and PCDFs.

TCDD has been found to be the most potent congener tested, capable of inducing the flat-cell effect at a concentration as low as $10^{-11}$ M. The activities of other tested PCDDs and PCDFs ranges from $10^{-1}$ to $10^{-3}$ of TCDD activity. The PCBs, PAHs, and pesticides have lower activities ranging from $10^{-3}$ to $10^{-6}$ that of TCDD.

There are 75 possible PCDD congeners and 135 possible PCDF congeners. The assay of this invention described herein demonstrates the correlation between chemical structure of these compounds and their biologic potency with regard to toxicity, enzyme induction, aryl hydrocarbon (Ah) receptor binding, and hyperkeratinization. The potency of these compounds is modulated by the positions halogenated, e.g. Br, Cl, I, and F.

The assay of this invention system using XBF cells cocultured with irradiated 3T3 fibroblast feeder cells, or other suitable non-proliferating fibroblast cells, or medium conditioned by proliferating or non-proliferating fibroblast cells, can be employed as an in vitro screening system for dioxinlike activity by testing benzene extracts of soot from a fire involving a PCB-containing transformer. The test procedures and results, described in the Examples, are compared to a high-resolution gas chromatographic/mass spectrometric analysis for total PCDFs in the same samples. The comparative data shows a good correlation, indicating that the XBF cell line of this invention is useful as a basis for a semiquantitative bioassay for dioxinlike activity.

The following detailed description, given by way of example, will best be understood in conjunction with the accompanying drawings, described as follows.

DETAILED DESCRIPTION OF CERTAIN PREFERRED EMBODIMENTS

EXAMPLE 1

Chemicals

Figure 1:
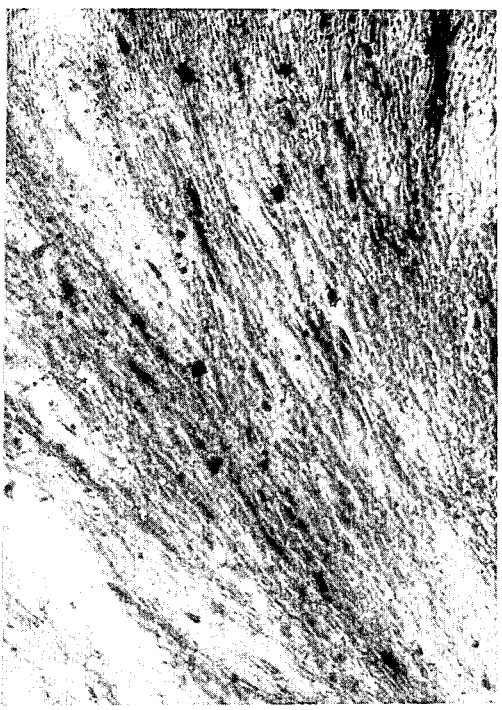
FIG. 1 illustrates dense packing and multilayering of control XBF/3T3 cultures, Giemsa stain, 100X magnification.

TCDD was obtained from Dow Chemical (Midland, Mich.). Purity was determined by mass spectrometry to be greater than 99%. The XB teratoma-derived mouse epithelial cells and the 3T3 fibroblast feeder cells were provided by Dr. Howard Green (Harvard University). Analytical grade dimethyl sulfoxide (DMSO) was obtained from the Aldrich Chemical Co. (Milwaukee, Wis.).

Cell Culture

XB cell stocks were grown in Costar plastic tissue culture flasks (75 cm$^2$) in Dulbeccos Modified Eagle Medium (DMEM; Gibco) supplemented with 20% fetal bovine serum (Flow, Rockville, Md.), 100 U of penicillin/ml, and 100 μg of streptomycin/ml. This medium had been conditioned by exposure to a confluent culture of 3T3 feeder cells for 24 hours (25ml of medium 75 cm$^2$ flask) and sterilized by filtration. The 3T3 feeder cells stocks were grown in DMEM supplemented with 10% calf serum (Flow).

The XB cells were routinely propagated every 1 to 2 weeks, when confluency was reached, by trypsinization (0.25%) and replating at a concentration of $2 \times 10^4$ cells per cm$^2$. The culture medium was renewed once a week between passages. The confluent density of these early XB cultures was about $4\times10^4$ cells per cm$^2$ under these conditions. These cells, when seeded with lethally irradiated 3T3 cells, were found to exhibit the TCDD-induced keratinization response as described by Knutson and Poland in Cell 22, 27–36, 1980. The magnitude of this keratinization response to TCDD exposure gradually declined after passage seven, and by passage 15, this response was greatly reduced compared to the early passage XB cells, although the sensitivity of this reduced response to TCDD was similar to that of the early passage cells. At this time the XB stock cultures, which were originally flat and polygonal, now had become more fusiform in morphology and reached confluency earlier than the low passage XB cultures. This alteration in growth and morphology at high density progressed during the next five to seven passages as the keratinization response to TCDD exposure disappeared. The confluent density of the cells at this time was about $15\times10^4$ cells per cm$^2$.

At this time it was discovered that medium conditioned by exposure to 3T3 cells was no longer required for the growth of these cells, which were now designated XBF to indicate their divergence from the XB line. Subsequently, stock cultures of XBF cells were routinely grown in non-conditioned DMEM supplemented with 20% fetal bovine serum (Flow). 100 U of penicillin/ml, and 100 $\mu$g of streptomycin/ml. The cultures were propagated by suspension in trypsin (0.25%), replated at a density of $3\times10^4$ cells per cm$^2$ once or twice a week as confluency was reached, and incubated at 37° C. in a humidified atmosphere of 5% $CO_2$.

Exposure Of Cells To TCDD

XBF cells were suspended by trypsinization and seeded into 24-well plates (16-mm-diameter wells, $5\times10^4$ cells per ml per well) in conditioned medium with 3T3 cells ($5\times10^5$ per ml per well) which had been lethally irradiated with 6000 rads from a cesium source. The cultures were incubated overnight and refed with a series comprising 10-fold dilutions of a stock solution of TCDD in DMSO or with DMSO alone in DMEM supplemented with 20% fetal bovine serum. This refeeding was repeated every 3 or 4 days for the duration of the experiment. The highest cumulative DMSO concentration was 0.1%.

At the end of incubation the cultures were washed with phosphate-buffered saline (PBS), fixed with formalin in PBS, and stained with Giemsa. Alternatively, the cultures were suspended by trypsinization at varying times after the initial exposure to TCDD. After thorough disaggregation of the cells by trituration, the number of cells per culture was determined with a Coulter Particle Counter (Coulter Instrument, Hialeen, Fla.). Complete disaggregation was confirmed by microscopic examination of the cell suspension immediately before counting. ($^3$H) Thymidine (New England Nuclear; specific activity=0.67 $\mu$Ci/mmol) incorporation at various times after exposure to TCDD was determined by pulse-labeling the cultures for the indicated times and counting the acid precipitable radioactivity in a Packard Tricarb liquid scintillation spectrometer as taught in Ellem and Gierthy, J. Cell Physiol. 92, 381–400, 1977. Autoradiography was performed as described in Ellem and Gierthy, J. Cell. Physiol. 92, 381–400, 1977.

Cell viability was determined by measuring the percentage of trypsin-suspended cells capable of excluding 0.1% trypan blue dye. Cloning efficiency was determined by seeding 200 cells in 5 ml of medium into a 60-mm plastic tissue-culture Petri dish (Falcon) and incubating for 2 weeks. Cultures were then washed i PBS, fixed in 10% formalin, and stained with Giemsa, and colonies were counted. Absolute cloning efficiency was defined as the percentage of the cells seeded capable of forming colonies.

Induction of Morphological Change in XBF Cells By Exposure to TCDD

Figure 2:
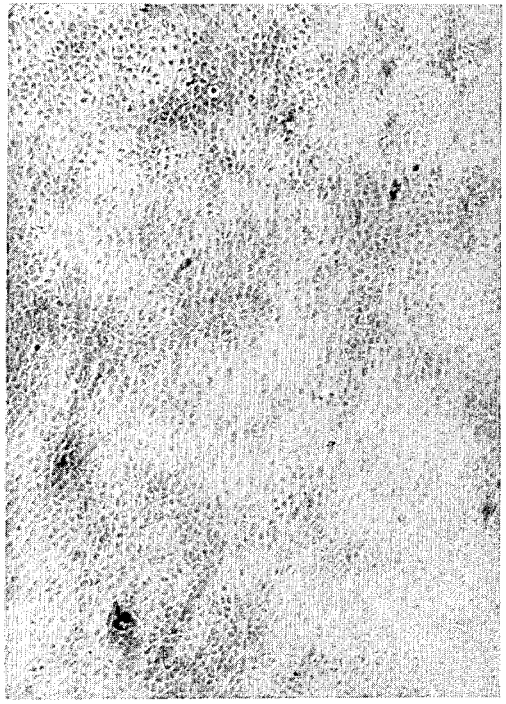
FIG. 2 illustrates induction of density-dependent inhibition of cell proliferation and flat-cell morphology characteristic of XBF/3T3 cultures after 14 days of exposure to $10^{-9}$ M TCDD, giemsa stain, 100X magnification.

The XBF cells, cocultured with irradiated 3T3 cells for 14 days, grew to very dense cultures characterized by apparent multilayering and the appearance of parallel growth patterns indicative of a spindlelike morphology. Treatment with 0.1% DMSO had no effect on this morphology (FIG. 1). Cultures grown in the presence of 10$^{-9}$M TCDD grew to confluency, and after 7 to 10 days began to develop into a cobblestone line monolayer comprised of flat, evenly distributed cells very apparent by day 14 (FIG. 2). Cultures of irradiated 3T3 feeder layer cells, seeded from the same stock used for these experiments, did not show any indication of growth or TCDD-induced morphological change. By day 14 these cultures had essentially disintegrated.

Figure 6:
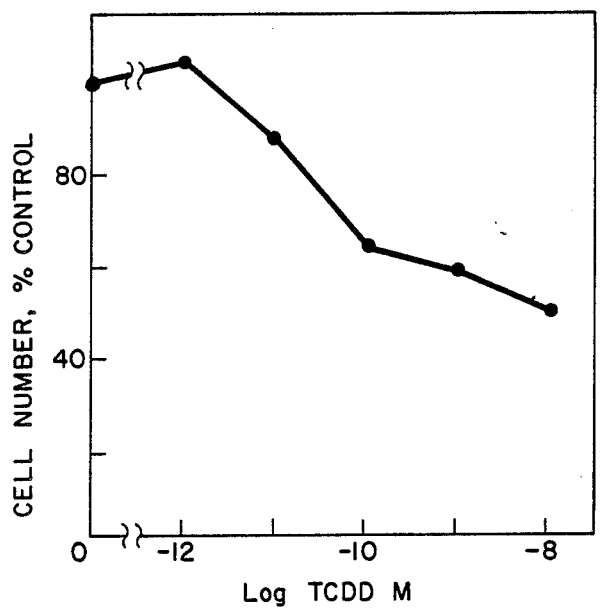
FIG. 6 illustrates the effect of TCDD on cell growth in XBF cultures. XBF cells seeded with irradiated 3T3 feeder cells and incubated. Medium replaced 24 hr after seeding and every 3 or 4 days thereafter with medium containing the indicated concentrations of TCDD in DMSO or DMSO alone. The cultures were trypsinized after 14 days, and cell number per culture well was determined. The data points represent the percentage of cells in the TCDD-treated cultures compared to control cultures and are the mean of four replicate cultures.

This change in growth and morphology was induced by TCDD concentrations ranging from 10$^{-9}$ to 10$^{-10}$M, the highest concentration tested. This dose-response effect was apparent in unmagnified, stained preparations (FIGS. 3 and 4), as well as in the number of cells in each culture after 14 days of exposure (FIG. 6). Solvent control cultures treated with DMSO at concentrations corresponding to those in the dilutions did not show this effect. The presence of 0.1% DMSO did not effect the TCDD dose-response. The ability of TCDD to induce these changes in morphology and growth in XBF cells has remained stable for over a year of cell passage as described in this Examples Section entitled: Cell Culture, supra.

Reduction In Cell Growth During Exposure to TCDD

Figure 7:
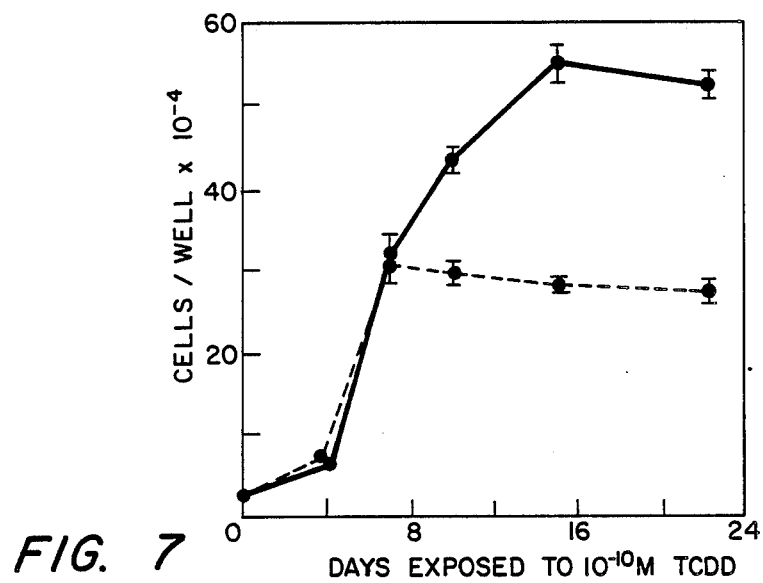
FIG. 7 represents the effect of TCDD on XBF cell proliferation kinetics. XBF cells were seeded and incubated with irradiated 3T3 feeder cells. Medium was replaced after 24 hours and every 3 or 4 days thereafter with medium containing TCDD with DMSO or DMSO alone. At the indicated times of exposure, the cultures were trypsinized, and cell number per culture well was determined. ●————● XBF/3T3, 0.01% DMSO; ●-----● XBF/3T3, $10^{-10}$ M TCDD, 0.01% DMSO; data points represent the mean of four replicates ±SE.
Figure 8:
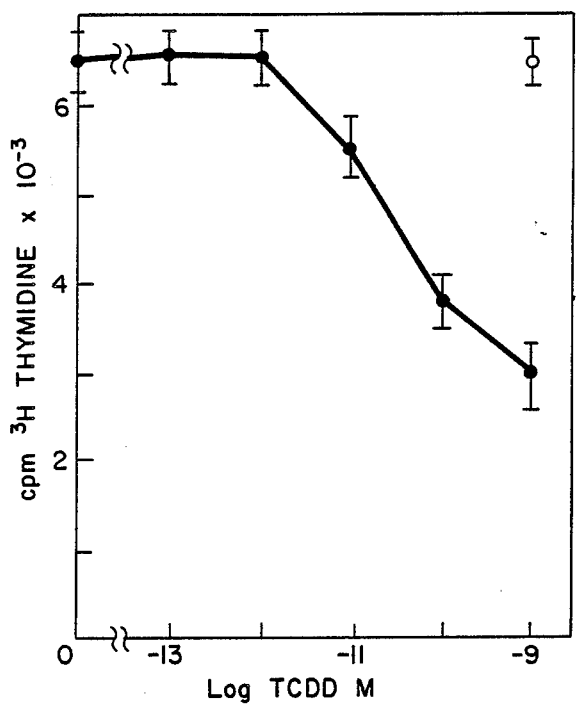
FIG. 8 represents the effect of TCDD on incorporation of ($^3$H) thymidine into XBF cells. XBF cells seeded with irradiated 3T3 cells and incubated. Medium was replaced after 24 hours and after 4 days with medium containing the indicated concentration of TCDD. On day 7 all cultures had reached confluency and had the same number of cells. At this time the cultures were pulse-labeled with ($^3$H) thymidine (0.5 uCi/ml, 6.7 Ci/mmol) for 1 hour, fixed, and counted for radioactivity. A DMSO concentration of .1% was the highest used in this experiment (0). Data points represent counts per minute $\times 10^{-3}$ per 16 mm culture well and are the mean of four replicates ± SE.

Investigation of the kinetics of cell growth in exposed cultures revealed that the decline in cell proliferation after TCDD exposure was not immediate. Cultures were seeded below confluency, as described in this Examples Section entitled: *Induction of Morpholopic Change in XBF Cells by Exposure to TCDD*, supra and after 24 hours were treated with 10$^{-9}$M TCDD and DMSO (0.1%) or with DMSO alone. FIG. 7 shows that both treated and untreated cultures accumulated cells at equal rates until day 7, at about which time confluency was reached. After this time the solvent control cultures continued to increase in cell number, while the TCDD-treated cultures did not. This cessation of cell proliferation is apparently TCDD-induced, as reflected in the TCDD-concentration-dependent decline in ($^3$H) thymidine incorporation into the acid-insoluble fraction of treated cultures (FIG. 8). This experiment was done after 7 days of exposure to TCDD, at which time the cultures had reached confluency, and the cell numbers were the same per culture. The range of TCDD concentrations capable of diminishing ($^3$H) thymidine incorporation corresponds to that which caused the morphological change and is supportive of the decline in DNA synthesis which would be expected to occur with the observed inhibition of cell growth. Further evidence that the lack of increase in cell number was due to a cessation of cell division, rather than to the TCDD-treated cells simply sloughing off resulting in a steady-state, was a decrease in the number of cells incorporating ($^3$H) thymidine into DNA, as shown by autoradiography. A 6 hour pulse with ($^3$H) thymidine at day 6, when the treated and untreated cultures showed equal growth rates, resulted in 45±4.4% of the cells being labeled. By day 13 of treatment the cultures exposed to $10^{-9}$ TCDD showed a reduction in labeling to 1.6 ±1.2%.

The viability of cells from these treated cultures was tested by trypan blue exclusion, which indicated a high viability of 87 ±2.5% in the $10^8$M TCDD-treated cultures, 85 ±4.2% in control cultures (0.1% DMSO), and 88 ±4.1% in untreated cultures. Cells from these cultures gave plating efficiencies of 33 ±3.6% for $10^{-8}$M TCDD-treated cultures, 37 ±6.3% for control cultures, and 34 ±4.5% for untreated cultures.

Figure 3:
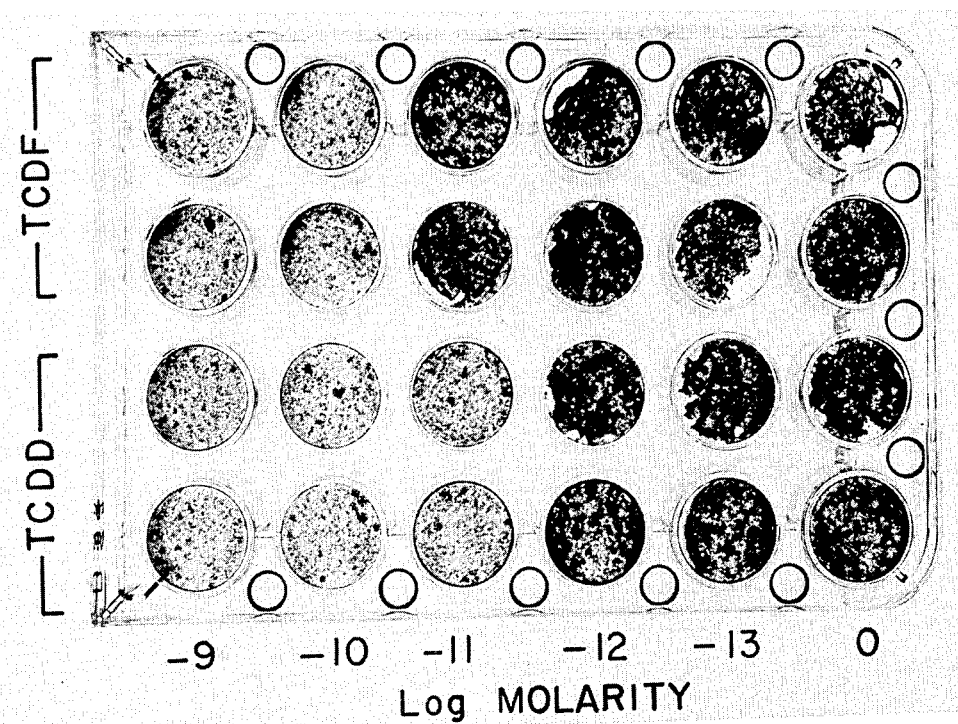
FIG. 3 illustrates the dose-response relation of flat-cell induction by 2,3,7,8-tetrachlorodiobenzo-p-dioxin (TCDD) and 2,3,7,8-tetrachlorodibenzofuran (TCDF) for the example in which XBF/3T3 cultures were exposed to indicated concentrations of TCDD and TCDF for 14 days, fixed, and stained with Giemsa stain. Less intensely stained, low-density cultures ($10^{-9}$ to $10^{-11}$ M for TCDD and $10^{-9}$ to $10^{-10}$ M for TCDF) exhibit the flat-cell morphology seen in FIG. 2. Flat-cell induction is first evident with $10^{-11}$ M TCDD and $10^{-10}$ M TCDF.
Figure 4:
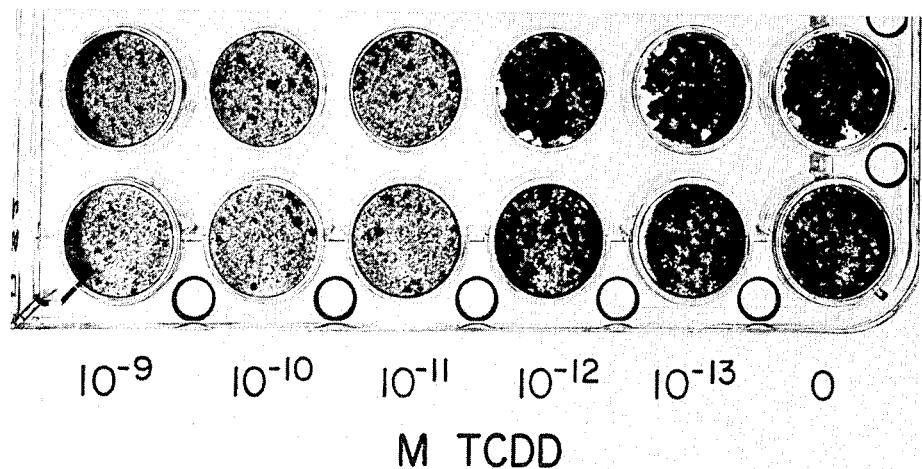
FIG. 4 illustrates dose-response relation of flat-cell induction by TCDD for the example in which XBF/3T3 cultures were exposed to various concentrations of TCDD as described in Example 1, Section entitled: *Exposure of Cells to TCDD*. After 14 days cultures were fixed and stained with Giemsa stain. Less intensely stained low-density cultures ($10^{-9}$ to $10^{-11}$ M) are similar to that shown in FIG. 2, while the intensely stained high-density cultures ($10^{-12}$, $10^{-13}$, and 0 M) are similar to that seen in FIG. 1. The flat-cell induction is first evident with $10^{-11}$ M TCDD.
Figure 9:
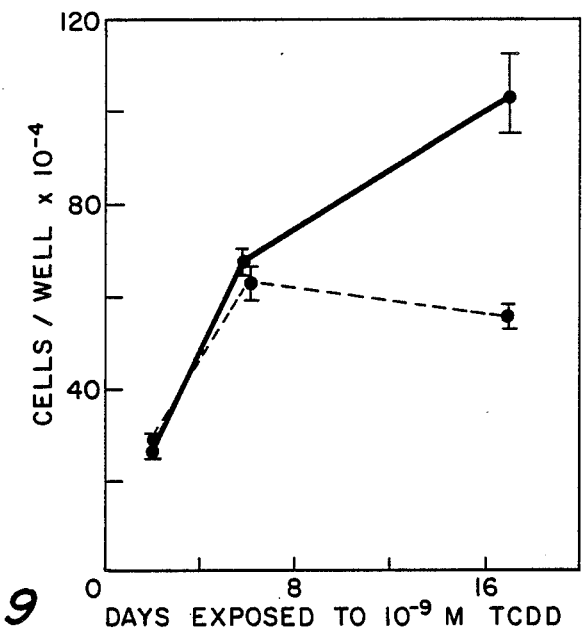
FIG. 9 represents the effect of TCDD on cell growth in XBF cultures of cells previously treated with TCDD. XBF cells, which had been exposed in the presence of irradiated 3T3 cells to $10^{-9}$ M TCDD for 14 days and exhibited growth inhibition and morphological changes, were seeded with fresh, non-TCDD-treated irradiated 3T3 feeder cells and incubated. Medium was replaced 24 hours after seeding and every 3 or 4 days thereafter with medium containing either $10^{-9}$ M TCDD in 0.01% DMSO or 0.01% DMSO. The cultures were trypsinized at the indicated times and the cell number per culture well was determined. ●————● XBF/3T3, 0.01% DMSO; ●--------● XBF/3T3, $10^{-9}$ M TCDD, 0.01% DMSO. Data points represent the mean of four replicates ±SE.

When cells treated with $10^{-9}$M TCDD for 14 days were suspended with trypsin, reseeded, and allowed to grow with or without added TCDD, again no difference in proliferation was seen until confluency was reached. At about this time TCDD-treated cells showed a decline in growth, while the untreated cells continued to proliferate to a higher saturation density (FIG. 9). The reduction in cell growth of these cultures of pretreated cells had the same sensitivity to TCDD ($10^{-11}$M) as cells which were not pretreated as seen by microscopic flat-cell evaluation and in the gross observation of fixed and stained cultures (FIG. 3).

Inhibition of Cell Division and The Morphological Change

Subconfluent XBF cells were treated with other inhibitors of proliferation, which have various mechanisms, to determine if the flat-cell morphology was a consequence of a general toxic effect related to inhibition of specific macromolecular synthesis. Inhibitors of DNA (hydroxyurea), RNA (actinomycin D), and protein (cycloheximide) synthesis, as well as the mitotic inhibitor cholchicine, were tested in 11 10-fold dilutions starting with a concentration of 100 µg/ml. The effects ranged from obvious toxicity, characterized by cell disintegration at the high concentrations, through inhibition of cell division, to no observable effects at the low ranges. The induction of a flat-cell morphology similar to that induced by TCDD in replicate XBF/3T3 cultures was not seen at any concentration of these agents.

EXAMPLE 2

Chemicals

TCDD was obtained from Dow Chemical (Midland, Mich.); its purity was determined by mass spectroscopy to be +99%. Other PCDDs and PCDFs (purity greater than 99%) were obtained from the National Institute of Environmental Health Sciences, the Illinois Institute of Technology, and Analabs (North Haven, CT). Single PCB isomers were obtained from Analabs at 99% purity. Commercial Acroclor 1254 was from Monsanto (St. Louis). PAHs were obtained from Aldrich Chemical (Milwaukee, WI). Eastman Organic (Rochester, NY), and K and K Laboratories (Plainview, NY) and recrystalized by B. Bush as taught by Choudhury and Bush. ANAL. CHEM. 53, 1351-1356, 1981. Pesticides were obtained as reference standards from the Environmental Protection Agency at greater than 99% purity. Analytical grade dimethyl sulfoxide ($ME_2SO$) was obtained from Aldrich Chemical Co.

Samples of soot were collected from the upper surfaces of ceiling panels on various floors of the Binghamton State Office Building (BSOB) in Binghamton, New York, after it was involved in a PCB-containing transformer fire.

Cell Culture

The XBF cells were derived from the cloned XB mouse epithelial cell line, which, along with the 3T3 feeder cells, was provided by H. Green, Harvard University. See Rheinwald and Green, Cell 6, 317-330, 1975. The derivation of the XBF line from the XB line is as described in detail Example 1 Section entitled: *Cell Culture*. XBF cells were routinely propagated once or twice a week, when confluency was reached, by trypsinization (0.25%) and replating at a concentration of $3 \times 10^4$ cells/cm². These cells were grown in Dubecco's modified Eagle medium (DMEM; Gibco) supplemented with 20% fetal bovine serum (Flow, Rockville, Md.), 100 U of penicillin/ml, and 100 µg of streptomycin/ml in a humidified atmosphere of 5% $CO_2$. The 3T3 feeder cell stocks were grown under the same incubation conditions in DMEM supplemented with 10% calf serum (Flow).

Assay Procedure

XBF cells were suspended by trypsinization and seeded into 24-well plates (16-mm-diameter wells, $5 \times 10^4$ cells per ml per well) with irradiated 3T3 cells ($5 \times 10^5$ per ml per well) in DMEM propagation medium conditioned by 24 hr exposure to confluent cultures of 3T3 cells (25 ml of medium per 75-cm² flask). After overnight incubation (37° C., 5% $CO_2$, humidified) the cultures were refed with a series of 10-fold dilutions of a stock solution of test chemical or soot extract in $ME_2SO$, or with $ME_2SO$ alone, in nonconditioned DMEM supplemented with 20% fetal bovine serum. Soxhlet benzene extracts of soot samples from the BSOB were produced and solvent-exchanged to $ME_2SO$. These extracts were diluted 1:1000 in the culture medium before the 10-fold dilutions were made. The medium containing the sample extract or test chemical was replaced every 3 or 4 days with freshly prepared dilutions. The highest cumulative $ME_2SO$ concentration was 0.1%. After 14 days the culture was assessed for flat-cell induction, washed with phosphate-buffered saline (PBS), fixed with formalin in PBS, and stained with either Giemsa or 1% rhodamine B in water.

The cultures were evaluated for the flat-cell effect by phase-microscopic assessment and confirmation that the tested cultures had grown to form a confluent monolayer of morphologically flat-cells as compared to the high density, control cultures comprised of multilayered fusiform cells as described in detail previously. Microscopic evaluation of staining intensity, i.e. an indication of cell culture density, was then made on the fixed and stained cultures as shown previously for TCDD and in FIG. 3 for TCDF as compared to the TCDD calibration standard.

RESULTS

Validation Of Flat-Cell Assay

The effects of a series of 10-fold dilutions of the TCDD standard and tetrachlorodibenzofuran (TCDF)

on XBF/3T3 cultures exposed and stained with Giemsa stain are shown in FIG. 3. The lightly stained wells correspond to the flat-cell, low saturation density appearance as described previously. The intensity of the staining can be used as an indicator of the flat-cell effect. Here, the TCDF exposure has an endpoint to $10^{-10}$ M, while that of TCDD is $10^{-11}$ M, indicating that TCDD is approximately 10-fold more potent.

For a series of 24 chemicals, including PCDDs, PCDFs, PCBs, PAHs, and pesticides, there was at least a 63-million-fold range in the potential for inducing the flat-cell effect as reported hereafter in Table 1 of this Example. These data show that the flat-cell effect is most sensitive to the more toxic PCDDS and PCDFs, with TCDD the most potent. Specifically 1, 2, 4, 7, 8-penta-CDD, which lacks chlorination in a lateral position of one of the benzene rings, shows 100-fold less activity than TCDD. TCDF was the most potent PCDF congener tested with flat-cell-inducing activity an order of magnitude lower than that of TCDD. Other PCDFs tested gave a range of activity, with hexa-CDF more potent than octa- or di-CDF. The rate of potency observed for the PCDDs and PCDFs tested, relative to TCDD, was about 1,000-fold. In contrast the various PCBs tested were $10^4$–$10^6$ times less potent than TCDD.

The PAHs varied in activity relative to TCDD. Dibenzo(a,h)anthracene and benz(a)anthracene were about $10^3$ and $10^4$ times less potent than TCDD respectively. 3-Methylcholanthrene and benzo(a)pyrene were both toxic at concentrations which were insufficient to induce a flat-cell effect. Of the pesticides only Mirex induced the flat-cell response at the concentrations tested, and was $10^6$ times less active than TCDD.

Application to Binghamton State Office Building (BSOB) Soot Samples

Benzene extracts of 10 soot samples taken from above the ceiling tiles of different floors of the BSOB were tested for their ability to induce the flat-cell effect. Although flat-cell inducing activity was detected in all 10 samples as described hereafter in Table 2 of this Example, the minimum amount of soot-equivalent of the extract needed to induce this effect to greater than background levels varied from 0.3 to 114.2 μg.

Figure 5:
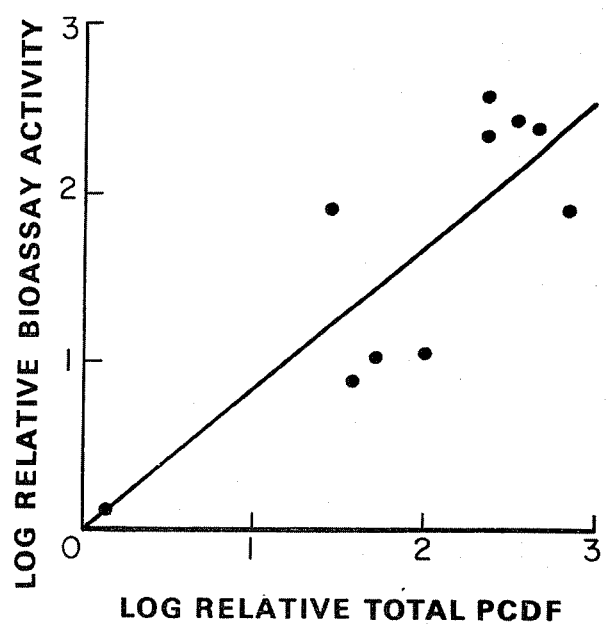
FIG. 5 represents a comparison of data for relative flat-cell induction described in Example 2, Table 2 entitled: Flat-Cell Inducing Activity of Binghamton State Office Building Soot Extracts and relative mass spectrometric analysis for polychlorinated dibenzofurans (PCDFs) for extracts of 10 soot samples from various floors of the Binghamton State Office Building. Both the relative flat-cell inducing activity and the relative total PCDF in each sample are plotted as a ratio to the value on floor 1. The correlation coefficient is 0.82.

These activities were compared to the total PCDF concentrations determined by GC/MS analysis for these samples in order to determine if these differences reflected actual variation in flat-cell inducing potential between samples. Total PCDF concentrations were used in this correlation, since, as predicted by pyrolysis studies of PCBs, see Buser et al., Chemosphere 7, 109–119, 419–429, 1978. PCDF concentrations in the soot were up to 100 times greater than those of the PCDDS. See Smith et al., Chemosphere 11, 715–720. The relative flat-cell-inducing activities as described hereafter in Table 2 of this Example, correlated well with the relative total PCDF concentrations of the various soot extracts (correlation coefficient, 0.82; FIG. 5).

TABLE 1

| Induction of the Flat-Cell Effect by Various Chemicals | |
|---|---|
| Compounds | Minimum Detectable Concentration (ppb) |
| 2,3,7,8-Tetrachlorodibenzo(p)dioxin | 0.0032 |
| 1,2,4,7,8-Pentachlorodibenzo(p)dioxin | 0.359 |
| 2,3,7,8-Tetrachlorodibenzofuran | 0.032 |
| 2,3,4,6,7,8-Hexachlorodibenzofuran | 0.378 |
| Octachlorodibenzofuran | 4.48 |
| 2,6-Dichlorodibenzofuran | +2.38 |
| 3,4,3',4'-Tetrachlorobiphenyl | 100 |
| 2,4,5,2',4',5'-Hexachlorobiphenyl | 1,000 |
| 2,5,2',5'-Tetrachlorobiphenyl | +10,000 |
| 2,3,4,2',4',5'-Hexachlorobiphenyl | +10,000 |
| 2,3,4,2',3',4'-Hexachlorobiphenyl | +10,000 |
| Aroclor 1254 | 10,000 |
| Dibenzo(a,h)anthracene | 10 |
| Benz(a)anthracene | 100 |
| 3-Methylcholanthrene | +100[a] |
| Benzo(a)pyrene | +100[a] |
| B—Naphthoflavone | 1,000 |
| Pyrene | +10,000 |
| Mirex | 10,000 |
| Dielarin | +10,000 |
| Aldrin | +10,000 |
| o,p'DDT | +10,000 |
| Lindane | +10,000 |
| BHC | +200,000 |

[a]Toxic concentration was 1,000 ppb.
Note: +×greater than

The experiments described hereinbefore and the corresponding results demonstrate the ability of the XBF flat-cell assay to detect flat-cell inducing activity in tested soot extracts and to discriminate between soot samples having relatively high and low levels of PCDFs as determined by GC/MS analysis.

The above Table 1 data illustrate that TCDF is about 10 times more potent in the flat-cell assay than 1,2,4,7,8-pentachlordibenzofuran and 2,3,4,6,7,8-hexachlorodibenzofuran. Other PCDF congeners tested are even less potent.

An important advantage of the XBF/3T3 cell line of this invention is its apparent sensitivity to the most toxic PCDDS and PCDFs. Data resulting from this in vitro system reflect the total dioxinlike activity associated within a sample, rather than quantitation of specific isomers, as in GC/MS, whose toxic potential may be unknown.

TABLE 2

| Flat-Cell-Inducing Activity of Binghamton State Office Building Soot Extracts | | |
|---|---|---|
| Floor | Endpoint (ug soot/ml)[a] | Relative Activity[b] |
| 1 | 114.2 | 1 |
| 4 | 1.4 | 82 |
| 6 | 15.9 | 7 |
| 7 | 0.3 | 381 |
| 8 | 10.0 | 11 |
| 9 | 1.5 | 76 |
| 10 | 0.5 | 228 |
| 14 | 12.9 | 9 |
| 15 | 0.4 | 284 |
| 17 | 0.4 | 284 |

[a]The average concentration of a series of 10-fold dilutions of extracts of soot from various floors of the Binghamton State Office Building capable of inducing a flat-cell effect greater than background. Each endpoint is replicates.
[b]Relative to activity of 1st-floor sample.

UTILITY

A practical use for the XBF/3T3 cell lines of this invention is to provide a cell line which can be employed in an economical and rapid biological assay for any substance having dioxinlike chemical activity.

Illustratively, a method, such as the following can be employed to identify negative samples, in terms of dioxinlike activity and cytotoxicity, for their separation from samples of concern, and allowing subsequent high resolution chemical analysis (HRCA) to be reserved for relevant samples which do exhibit dioxinlike activity.

Step 1:

24 hr benzene extraction of all organics of an assay sample in a closed container at room temperature. Evaporation of benzene extract to a volume of 5 ml. Solvent exchange of 1 ml of this extract, without drying, to 30 ul with dimethyl sulfoxide (DMSO). The DMSO solution is applied to the XBF/3T3 culture system for detection of biological activity as described in the Example 2 Section entitled: Assay Procedure.

If no effect is detected, the sample is considered to have no dioxinlike activity or cytotoxicity above the predetermined limits of detection and the sample may be considered to be of low priority or removed from further testing procedures. A positive response indicates cytotoxcity and/or dioxinlike activity which may be caused by dioxinlike compounds or relatively high levels of less potent polynuclear aromatic hydrocarbons (PNAHs).

Step 2

Samples which exhibit a biological effect in Step 1 are further investigated to determine if the effect is characterized by (a) general cytotoxicity and/or dioxinlike activity from non dioxinlike compounds, e.g. high concentrations of PNAHs of low dioxinlike activity potential or (b) dioxinlike activity associated with dioxinlike compounds. The remaining 80% (4 ml) of the original benzene extract is subjected to the multicolumn and basic alumina cleanup to remove cytotoxic compounds and PNAHs with their associated dioxinlike activity.

Step 3:

One ml of the sample extract from Step 2 is then subjected to the flat-cell assay (FCA) for demonstration of dioxinlike activity. If this assay is negative, the original activity seen in Step 1 is most likely to be caused by non-dioxinlike compounds. At this stage an appropriate method for chemical analysis can be rationally applied in order to identify any organic compounds which might be responsible for the activity in the first bioassay.

The method of chemical analysis is dependent on a number of factors including the particular site and the probability of finding certain compounds, i.e., PNAHs in any sample. In any case the instrumental requirements for the analysis could be met by either high or low resolution mass spectrometry. A positive FCA on the cleaned up extract indicates that the dioxinlike activity of the sample is caused by a dioxinlike compound(s).

This second FCA includes 5- tenfold dilutions of the extract, thus generating semi-quantitative results.

This level of analysis is sufficient for initial regulatory or health considerations and actions, depending on the level of activity found.

Step 4:

This step determines the concentration and identity of the specific dioxinlike isomer or congener that induced any dioxinlike activity in Step 3 and requires high resolution chemical analysis using gas chromatographic/mass spectrometric capabilities. The remaining 60% (3 ml) of the extract to be used in this step has already been subjected to adequate cleanup for such analysis. A decision can be made based upon the semi-quantitative results of the FCA as to the type of mass spectrometric analysis to be done. Samples in which activity equivalent to 10 ngm of material or more is detected are analyzed by either the low or high resolution mass spectrometer. By acquiring full mass spectra in extract components as they elute from the gas chromatograph an identification of the chemical entities in the extract is made. This insures the rapid identification of dioxinlike compounds in samples which are not contaminated with dioxinlike compounds. A second advantage is the splitting of the sample load among more than one instrument. Samples in which less than 10 ngm but more than 100 pgm are detected can be analyzed by either type of mass spectrometer, thus again splitting the workload.

In implementing this assay, it is important to note that this scheme will allow negative samples (i.e. those with no dioxinlike activity or general toxicity as shown in Step 1) to be processed at a significant savings in time and money compared to the amount of time and money required for processing by HRGC/MS. The actual time and money savings on any screening program following the method of this invention would be dependent on the probability of finding dioxinlike compounds at a specific site, and on the amount of isomer specific data appropriate for the purpose of the screen.

The flow diagram set in Table 3 which follows summarizes the general outline of the sequence of steps set out above.

TABLE 3

Bioassay Priority Ranking Scheme for Dioxinlike Activity (DLA) in Toxic Site Samples

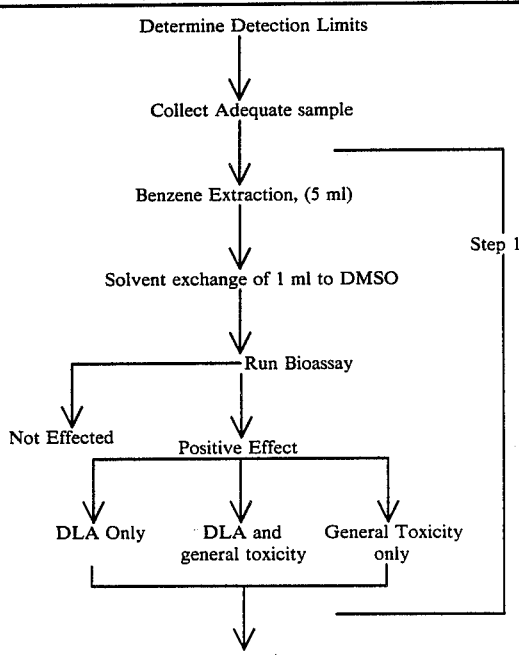

TABLE 3-continued
Bioassay Priority Ranking Scheme for Dioxinlike Activity (DLA) in Toxic Site Samples

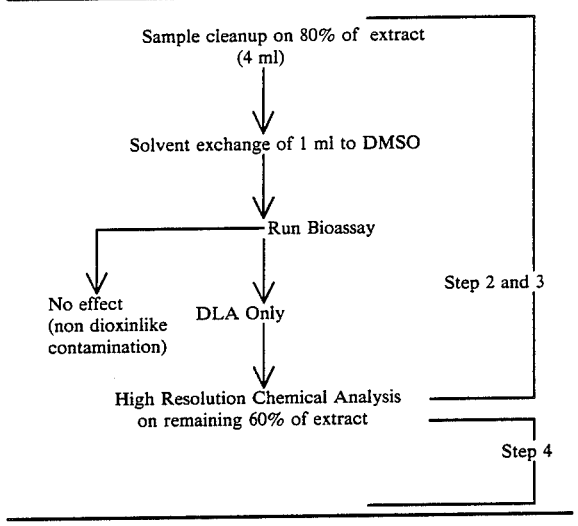

The terms and expressions which have been employed are used in terms of description and not of limitation, and there is no intention in the use of such terms and expressions of excluding any equivalents of the features shown and described or portions thereof, it being recognized that various modifications are possible within the scope of the invention.

While the present invention has been particularly described with respect to certain preferred embodiments, various changes and modifications will be readily apparent to those of ordinary skill in the art without departing from the spirit and scope of the invention. The present invention should not be limited solely to the described embodiments. Rather, the appended claims should be interpreted to cover the aforesaid changes and modifications and equivalents.

What is claimed is:

1. A non-keratinizing epithelial cell line which has the characteristics of ATCC CRL 8808 wherein the characteristics comprise a low saturation density, flat-cell morphology and inhibition of post-confluent cell proliferation when exposed to polychlorinated dibenzodioxins or polychlorinated dibenzofurans or their structural analogs which exhibit biological activity characteristic of polychlorinated dibenzodioxins or polychlorinated dibenzofurans, when cultured with a culturing means selected from the group consisting of non-proliferating fibroblast cells, a medium conditioned by non-proliferating fibroblast cells, and lethally irradiated 3T3 fibroblast cells, which biological activity comprises a low saturation density, flat cell morphology and inhibition of post-confluent cell proliferation.

2. A method of producing a non-keratinizing epithelial cell line as defined in claim 1, which comprises
propagating XB epithelial cells in the presence of a propagating means selected from the group consisting of non-proliferating fibroblast cells, a medium conditioned by non-proliferating fibroblast cells, and lethally irradiated 3T3 fibroblast cells, and
subculturing the propagated epithelial cells until the propagating means is no longer required for continued propagation.

3. A method of producing a non-keratinizing epithelial cell line as defined in claim 17, wherein the propagating means is non-proliferating fibroblast cells.

4. A method of producing a non-keratinizing epithelial cell line as defined in claim 17 wherein the propagating means is a medium conditioned by non-proliferating fibroblast cells.

5. A method of producing a non-keratinizing epithelial cell line as defined in claim 17, wherein the propagating means is lethally irradiated 3T3 fibroblast cells.

6. A method of detecting, in a sample, the presence of polychlorinated dibenzodioxins and polychlorinated dibenzofurans and their structural analogs which exhibit biological activity characteristic of polychlorinated dibenzodioxins and polychlorinated dibenzofurans which activity comprises a low saturation density, flat cell morphology and inhibition of post-confluent cell proliferation in the sample, which method comprises
culturing a non-keratinizing epithelial cell line as defined in claim 1 with a culturing means selected from the group consisting of non-proliferating fibroblast cells, a medium conditioned by non-proliferating fibroblast cells, a medium conditioned by proliferating fibroblast cells, and lethally irradiated 3T3 fibroblast cells which causes the culture to react characteristically to the presence of polychlorinated dibenzodioxins and polychlorinated dibenzofurans and their structural analogs which exhibit biological activity characteristic of polychlorinated dibenzodioxins and polychlorinated dibenzofurans,
contacting the culture with the sample, and
examining the contacted culture for the exhibition of characteristics indicative of the presence of polychlorinated dibenzodioxins and polychlorinated dibenzofurans and their structural analogs which exhibit biological activity characteristic of polychlorinated dibenzodioxins and polychlorinated dibenzofurans which characteristics comprise a low saturation density, flat cell morphology and inhibition of post-confluent cell proliferation, as compared to a non-contacted control culture which exhibits high saturation density fusiform morphology and post-confluent cell proliferation.

7. A method as defined in claim 6, wherein the culturing means is non-proliferating fibroblast cells.

8. A method as defined in claim 6, wherein the culturing means is a medium conditioned by non-proliferating fibroblast cells.

9. A method as defined in claim 6, wherein the culturing means is a medium conditioned by proliferating fibroblast cells.

10. A method as defined in claim 6, wherein the culturing means is lethally irradiated 3T3 fibroblast cells.

11. A method as defined in claim 6, wherein the characteristics indicative of the presence of dioxin and related compounds which exhibit characteristic dioxinlike activity are a low saturation density, flat-cell morphology and inhibition of post-confluent cell proliferation, as compared to a non-contacted control culture.

12. A method of detecting, in a sample, the presence of polychlorinated dibenzodioxins and polychlorinated debenzofurans and their structural analogs which exhibit biological activity characteristic of polychlorinated dibenzodioxins and polychlorinated debenzofurans which activity comprises a low saturation density, flat cell morphology and inhibition of post-confluent cell proliferation in the sample, which comprises culturing non-keratinizing XHF epithelial cells with lethally irradiated 3T3 fibroblast cells to form an XBF/3T3 culture, contacting the XBF/3T3 culture with the sample, examining the contacted culture for the exhibition of characteristic low saturation density, flat-cell morphology and inhibition of post-confluent cell proliferation, as compared to a non-contacted control culture which exhibits high saturation density, fusiform morphology and post-confluent cell proliferation.

13. A method of detecting, in a sample, the presence of polychlorinated dibenzodioxins and polychlorinated dibenzofurans which comprises culturing non-keratinizing XBF epithelial cells with lethally irradiated 3T3 fibroblast cells to form an XBF/3T3 culture, contacting the XBF/3T3 culture with the sample, examining the contacted culture for the exhibition of low saturation density, flat-cell morphology and inhibition of post-confluence cell proliferation which are characteristics indicative of the presence of polychlorinated dibenzodioxins and polychlorinated dibenzofurans.

* * * * *

UNITED STATES PATENT AND TRADEMARK OFFICE
CERTIFICATE OF CORRECTION

PATENT NO. : 4,904,595

DATED : February 27, 1990

INVENTOR(S) : John J. Gierthy

It is certified that error appears in the above-identified patent and that said Letters Patent is hereby corrected as shown below:

Claim 3, line 2, column 18, line 2, delete "17" and insert --1--.

Claim 4, line 2, column 18, line 5, delete "17" and insert --1--.

Claim 5, line 2, column 18, line 9, delete "17" and insert --1--.

Claim 6, line 34, column 18, line 45, after "density" insert a comma (,).

Claim 12, line 3, column 18, line 65, delete "debenzofurans" and insert --dibenzofurans--;

lines 5 and 6, column 18, lines 68 and 69, delete "debenzofurans" and insert --dibenzofurans--;

Claim 12, line 9, column 19, line 3, delete "XHF" and insert --XBF--.

Signed and Sealed this

Thirteenth Day of August, 1991

*Attest:*

HARRY F. MANBECK, JR.

*Attesting Officer*      *Commissioner of Patents and Trademarks*